US012295929B2

(12) United States Patent
Cloyd et al.

(10) Patent No.: US 12,295,929 B2
(45) Date of Patent: *May 13, 2025

(54) INTRAVENOUS BACLOFEN FORMULATIONS AND TREATMENT METHODS

(71) Applicants: Allaysis, LLC, Weston, FL (US); Regents of the University of Minnesota, Minneapolis, MN (US)

(72) Inventors: James C. Cloyd, Minneapolis, MN (US); Adolfo L. Gomez, Sticklerville, NJ (US); Linda Krach, Minneapolis, MN (US); Robert L. Kriel, Minneapolis, MN (US); John Schrogie, Lansdale, PA (US); Stephen John Tucker, Chester, PA (US); Rob Tuohy, Philadelphia, PA (US)

(73) Assignees: ALLAYSIS, LLC, Weston, FL (US); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/136,777

(22) Filed: Apr. 19, 2023

(65) Prior Publication Data

US 2023/0248679 A1 Aug. 10, 2023

Related U.S. Application Data

(60) Continuation of application No. 17/164,366, filed on Feb. 1, 2021, now abandoned, which is a division of application No. 16/458,994, filed on Jul. 1, 2019, now Pat. No. 10,933,042, which is a division of application No. 14/997,135, filed on Jan. 15, 2016, now Pat. No. 10,350,183.

(60) Provisional application No. 62/103,902, filed on Jan. 15, 2015.

(51) Int. Cl.
| | | |
|---|---|---|
| A61K 31/197 | (2006.01) | |
| A61K 9/00 | (2006.01) | |
| A61K 45/06 | (2006.01) | |
| A61P 25/14 | (2006.01) | |

(52) U.S. Cl.
CPC .......... *A61K 31/197* (2013.01); *A61K 9/0019* (2013.01); *A61K 45/06* (2013.01); *A61P 25/14* (2018.01)

(58) Field of Classification Search
None
See application file for complete search history.

(56) References Cited

U.S. PATENT DOCUMENTS

| | | |
|---|---|---|
| 5,091,184 A | 2/1992 | Khanna |
| 5,192,797 A | 3/1993 | Raizon et al. |
| 6,969,383 B2 | 11/2005 | Hildebrand |
| 8,357,379 B2 | 1/2013 | Trissel et al. |
| 10,350,183 B2 | 7/2019 | Cloyd et al. |
| 10,933,042 B2 | 3/2021 | Cloyd et al. |
| 2006/0089335 A1 | 4/2006 | Liu et al. |
| 2013/0012586 A1 | 1/2013 | Roberts et al. |
| 2013/0109755 A1 | 5/2013 | Schmitz et al. |
| 2016/0213631 A1 | 7/2016 | Cloyd et al. |
| 2020/0038353 A1 | 2/2020 | Cloyd et al. |
| 2021/0228520 A1 | 7/2021 | Cloyd et al. |

FOREIGN PATENT DOCUMENTS

| | | |
|---|---|---|
| WO | 2001026638 A2 | 4/2001 |
| WO | 2008066750 A1 | 6/2008 |
| WO | 2013180796 A1 | 12/2013 |

OTHER PUBLICATIONS

Scherkenbach et al (Journal of Pharmacy and Pharmacology 66:935-942, published online Feb. 13, 2014) (Year: 2014).*
Coffey, R., et al., "Abrupt Withdrawal From Intrathecal Baclofen: Recognition and Management of a Potentially Life-Threatening Syndrome", Arch Phys Med Rehabil 83, 735-741 (2002).
Schmitz, N., et al., "Characterizing Baclofen Withdrawal: A National Survey of Physician Experience", Pediatric Neurology 122, 106-109 (2021).
Terrence, C., et al., "Complications of Baclofen Withdrawal", Arch Neurol 38, 588-589 (1981).
Australian Product Information—available online at https://medicines.org.au/files/txpbaclo.pdf, accessed Dec. 17, 2019 (2019).
Agarwal, S., et al., "A pilot study assessing pharmacokinetics and tolerability of oral and intravenous baclofen in healthy adult volunteers", J Child Neurol 30(1), 37-41 (2015).
Brennan, P., et al., "Intrathecal baclofen therapy for neurological disorders: a sound knowledge base but many challenges remain", British Journal of Neurosurgery 22 (4), 508-519 (2008).
Gottula, A., et al., "Dexmedetomidine for Acute Management of Intrathecal Baclofen Withdrawal", The Journal of Emergency Medicine 58 (1), e5-e8 (2020).
Government of South Australia, "Policy Clinical Guideline, Intravenous to Oral Switch Guideline for Adults Patients—can antibiotics S.T.O.P.", Department of Health and Ageing, Objective file No. 2014-06571, 3 pages (2015).
Hachen, et al., "Clinical and Laboratory Assessment of the Efficacy of Baclofen (Lioresal®)on Urethral Sphincter Spasticity in Patients with Traumatic Paraplegia", Eur Urol 3(4), 237-240 (1977).
Henry, J., "Effects of intravenously administered enantiomers of baclofen on functionally identified units in lumbar dorsal horn of the spinal cat", Neuropharmacology 21 (11), 1073-1083 (1982).
Khanal, R., et al., "Severe Case of Oral Baclofen Withdrawal Resulting in Mechanical Ventilation", Journal of Investigative Medicine High Impact Case Reports 10, 1-3 (2022).
Krach, L., et al., "Clinical tolerance and toxicity of intravenous baclof en: A pilot study in a canine model", Journal of Pediatric Rehabilitation Medicine 4, 89-98 (2011).

(Continued)

*Primary Examiner* — Craig D Ricci
(74) *Attorney, Agent, or Firm* — Viksnins Harris Padys Malen LLP

(57) ABSTRACT

An intravenous baclofen solution is disclosed, along with methods of dosing and treatment therewith.

12 Claims, No Drawings

(56) References Cited

OTHER PUBLICATIONS

Kriel, R, et al., "Prevention of Baclogen Withdrawal Syndrome: Pharmacokinetics and Tolerability of Oral and Intravenous Baclofen in Healthy Adult Volunteers", Physical Medicine and Rehabilitation 6 (9S), S221-S222, Poster 110, (2014).
Larowe, B, et al., "In Support of Initial Parenteral Medical Management of Intrathecal Baclofen Withdrawal in Spasticity Patients", Journal of Pharmacy Technology 37(6), 293-297 (2021).
Romito, J, et al., "Baclofen therapeutics, toxicity, and withdrawal: A narrative review", SAGE Open Medicine 9, 1-13 (2021).
Sanders, B, et al., "Oral Baclofen Withdrawal Resulting in Hyperactive Delirium: A Case Report", Cureus13(5), e14979, DOI10.7759/cureus.14979, 3 pages (2021).
Scherkenbach, L, et al., "Pharmacokinetics and pharmacodynamics of intravenous baclofen in dogs: a preliminary study", Journal of Pharmacy and Pharmacology 66, 935-942 (2014).
Schmitz, "A Randomized Dose Escalation Study of Intravenous Baclofen in Healthy Volunteers: Clinical Tolerance and Pharmacokinetics", Physical Medicine and Rehabilitation 9(8), 743-750 (2017).
Sintetica, S, "Baclofen Intrathecal", DCP No. BE/H/152/03/DC, 1.3 Product Information, 1.3.1 SPC, Labelling and Package Leaflet, 1.3.1.1 SPC, CTD Module 1, Administrative Information and Prescribing Information, Baclogen Intrathecal, Version 5.0, (2010).
Sullivan, E, et al., "A Guide to Substance Abuse Services for Primary Care Clinicians", U.S. Department of Health and Human Services, Chapt 5 and Appendix A, 40 pages (2008).

\* cited by examiner

INTRAVENOUS BACLOFEN FORMULATIONS AND TREATMENT METHODS

CROSS-REFERENCE TO RELATED APPLICATIONS

This application is a continuation of U.S. patent application Ser. No. 17/164,366, filed Feb. 1, 2021, which is a divisional of U.S. patent application Ser. No. 16/458,994, filed Jul. 1, 2019, now U.S. Pat. No. 10,933,042, issued Mar. 2, 2021, which is a divisional of U.S. patent application Ser. No. 14/997,135, filed Jan. 15, 2016, now U.S. Pat. No. 10,350,183, issued Jul. 16, 2019, which claims the benefit of U.S. Provisional Application Ser. No. 62/103,902, filed 15 Jan. 2015. The entire content of the applications referenced above are hereby incorporated by reference herein.

BACKGROUND OF THE INVENTION

Baclofen is a muscle relaxant and anti-spastic agent. Spasticity is a common symptom of upper motor neuron injury in individuals with cerebral palsy, multiple sclerosis, acquired spinal cord injury, brain injury, and neurodegenerative disorders. Baclofen is a structural analog of the inhibitory neurotransmitter gamma-aminobutyric acid (GABA) and acts as a $GABA_B$ agonist at the level of the spinal cord. Baclofen is the generic name for 4-amino-3-(4-chlorophenyl) butanoic acid. It is a white or off-white, mostly odorless crystalline powder with a molecular weight of 213.66, and it is slightly soluble in water. Baclofen's structural formula is

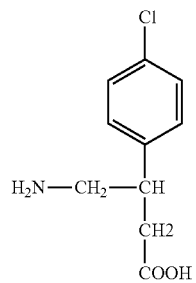

Baclofen is sold under the tradename LIORESAL® in oral (10 mg or 20 mg tablets) and intrathecal (0.05 mg/mL, 0.5 mg/mL, or 2.0 mg/mL) formulations. The intrathecal formulation is used in conjunction with an implanted programmable pump to provide a constant infusion of the drug. There are several circumstances in which patients treated with oral or intrathecal baclofen must abruptly discontinue therapy. For example, the programmable pump and/or catheter used in intrathecal administration may need to be removed, refilled, or replaced. Moreover, patients taking oral baclofen may be unable to do so during periods of illness, noncompliance, or surgery, for example. Abrupt discontinuation of oral or intrathecal baclofen can result in a severe withdrawal syndrome characterized by rebound increases in muscle tone and spasms, status epilepticus, hallucinations, and a neuromalignant syndrome-like picture potentially resulting in rhabdomyolysis and multisystem organ failure. The current recommended management of baclofen withdrawal is inadequate, and symptoms are often difficult to control. Agarwal et al., *A Pilot Study Assessing Pharmacokinetics and Tolerability of Oral and Intravenous Baclofen in Healthy Adult Volunteers*, J Child Neurol., (Jul. 14, 2014), http://jcn.sagepub.com/content/early/2014/07/11/0883073814535504.

Thus, there is a clinical need for an intravenous baclofen formulation to prevent or minimize complications resulting from interrupted oral or intrathecal therapy.

BRIEF SUMMARY OF THE INVENTION

An intravenous baclofen solution is disclosed, along with methods of dosing and treatment therewith. It is believed that intravenous administration of baclofen can permit rapid attainment of necessary drug concentrations, as well as accurate and precise dose titration, thereby allowing for more efficient and effective treatment of withdrawal symptoms or preventing withdrawal altogether.

One embodiment of the invention provides a method of temporarily treating a subject with baclofen during a period of medical fluctuation that comprises (a) discontinuing oral or intrathecal administration of baclofen to the subject; (b) administering to the subject a bolus intravenous dose of a therapeutically effective amount of a solution comprising baclofen at a concentration of up to about 2.0 mg/mL over a time period of about 5 minutes to about 60 minutes; (c) repeating administration of the bolus intravenous dose of baclofen about every 6 to 8 hours until oral or intrathecal administration of baclofen can be resumed; (d) discontinuing administration of bolus intravenous doses of baclofen; and (e) resuming oral or intrathecal administration of baclofen.

In another embodiment, a method of intravenously administering baclofen to a subject that has previously been treated with oral baclofen in a therapeutically effective amount comprises (a) discontinuing oral administration of baclofen to the subject; (b) administering to the subject a bolus intravenous dose of solution comprising about 75% of said amount of baclofen over a time period of about 5 minutes to about 60 minutes; (c) repeating administration of the bolus intravenous dose of baclofen about every 6 to 8 hours until oral administration of baclofen is resumed; (d) discontinuing administration of intravenous baclofen; and (e) resuming oral administration of baclofen.

In another embodiment, a method of temporarily treating a subject with baclofen during a period of medical fluctuation comprises (a) discontinuing oral or intrathecal administration of baclofen to the subject; (b) starting a continuous intravenous infusion of a therapeutically effective amount of a solution comprising baclofen at a concentration up to about 2.0 mg/mL over a time period of about 24 hours; (c) continuing the infusion about every 24 hours until oral or intrathecal administration of baclofen is resumed; (d) discontinuing the continuous intravenous infusion; and (e) resuming oral or intrathecal administration of baclofen.

In another embodiment, a method of intravenously administering baclofen to a subject that has previously been treated with oral baclofen in a therapeutically effective amount comprises (a) discontinuing oral administration of baclofen to the subject; (b) administering a continuous intravenous infusion of solution comprising about 75% of said amount of baclofen over a time period of about 24 hours; (c) continuing the infusion about every 24 hours until oral administration of baclofen is resumed; (d) discontinuing administration of the continuous intravenous infusion; and (e) resuming oral administration of baclofen.

In another embodiment, a method of converting an oral dose of baclofen to an intravenous dose of baclofen comprises (a) determining the oral dose; and (b) multiplying the oral dose by between about 0.45 and about 1.0 to determine the intravenous dose.

In another embodiment, a pharmaceutical solution comprises an effective therapeutic amount of up to about 2.0 mg/mL baclofen dissolved in at least one of normal saline, dextrose solution, Lactated Ringer's solution, or any combination thereof; wherein the solution is adapted to be intravenously administered to a subject.

DETAILED DESCRIPTION OF THE INVENTION

Each milliliter of intravenous baclofen solution can contain about 0.5 mg to about 2.0 mg of baclofen and an isotonic amount of sodium chloride dissolved in sterile water. In an embodiment, the concentration of baclofen in the intravenous solution can be about 0.5-2.0 mg/mL. In an embodiment, the intravenous baclofen solution can include a dextrose solution or Lactated Ringer's solution instead of or in combination with normal saline. The intravenous baclofen solution can further include an anticonvulsant drug, an antispasmodic drug, an anticholinergic drug, and/or an antibiotic.

The present invention also provides a correlation between oral and intravenous dosing of baclofen (see, e.g., Example 2 below). In particular, an equivalent dose of intravenous baclofen can be determined by multiplying the oral dose of baclofen by about 0.45 to about 1.0, preferably by about 0.6 to about 0.9, and more preferably by about 0.75.

Generally, an effective amount of the above-described intravenous baclofen solution can be administered intravenously to temporarily treat a patient during a period of medical fluctuation resulting in the discontinuation of oral or intrathecal baclofen. Temporary treatment with intravenous baclofen may be necessary as bridging therapy (e.g., when a patient is temporarily unable to take oral or intrathecal baclofen) or for management of withdrawal symptoms, for example. As used herein, a "period of medical fluctuation" refers broadly to a time period during which a patient experiences an illness, condition, change in health status, or situation requiring an adjustment to his/her normal medical care or treatment plan. More specifically, a period of medical fluctuation can include at least one of a scheduled or unscheduled surgical procedure, trauma, ileus, bowel obstruction, vomiting, diarrhea, gastrointestinal malabsorption, seizure, stroke, subarachnoid hemorrhage, or patient non-compliance. Furthermore, for patients with implanted intrathecal pumps, periods of medical instability can include an intrathecal hardware failure or a necessity to remove, refill, or replace the intrathecal hardware.

In one embodiment of the invention, a method is provided to temporarily treat a patient with intravenous baclofen during a period of medical fluctuation that comprises discontinuation of oral or intrathecal administration of baclofen to the patient, followed by administration of an intravenous bolus dose of a therapeutically effective amount of a baclofen solution (e.g., between about 1 mg and about 50 mg baclofen per bolus dose) over a time period of about 5 to 60 minutes. The intravenous bolus dose can be administered repeatedly about every 6 to 8 hours until oral or intrathecal administration of baclofen can be resumed. Once intravenous bolus doing has been discontinued, oral or intrathecal administration of baclofen can be resumed.

In another embodiment of the invention, a method of temporarily treating a patient with intravenous baclofen during a period of medical fluctuation is provided that can include discontinuation of oral or intrathecal administration of baclofen, followed by administration of a continuous intravenous infusion of a therapeutically effective amount of a baclofen solution continued until oral or intrathecal administration of baclofen can be resumed. Once continuous intravenous infusions have been discontinued, oral or intrathecal administration of baclofen can be resumed. It is believed that continuous intravenous infusion of baclofen can mimic intrathecal administration of baclofen, can eliminate or mitigate any peaks or troughs in baclofen levels in a patient's cerebral spinal fluid or blood (which may occur during intravenous bolus administration, for example), and can reduce the risk or incidence of adverse events associated with intravenous baclofen.

The invention will be further described by the following detailed examples.

Example 1—Preparation of Intravenous Baclofen Solution 108 g of sodium chloride were placed in a 600 ml beaker and then added to a 20 L beaker containing 8.4 L of sterile water for injection. The resulting sodium chloride solution was stirred in the 20 L beaker until dissolution occurred. Approximately 50 ml of sterile water for injection were used to rinse any residual sodium chloride from the 600 ml beaker, and the rinsings were added to the 20 L beaker. Next, 24.1 g of baclofen powder were placed in a 1 L beaker and then gradually (over a time period of about 2 hours) added and dissolved in the solution in the 20 L beaker. Approximately 50 ml of sterile water for injection was used to rinse any residual baclofen from the 1 L beaker, and the rinsings were added to the 20 L beaker. Approximately 3500 mL of sterile water for injection were then added to the 20 L beaker, and the solution was mixed for a minimum of 10 minutes to ensure homogeneity. The solution was then filtered using a Mini Kleenpak™ (0.2 µm) filter at 20 rpm.

An automated, aseptic filling machine was used to fill approximately 1090 13.5-mL glass vials with approximately 11.0 ml of the solution per vial. The vials were then stoppered, caps were placed on the vials, and the caps were crimped. The vials were stored at about 15 degrees Celsius to about 25 degrees Celsius.

Example 2—Administration of Intravenous Baclofen

A. Subjects

Twelve healthy human volunteers were recruited. The volunteers were medication free for 48 hours before, during, and 24 hours after the administration of the study drug.

B. Study Design

The 12 volunteers participated in a randomized, open-label, 2-way crossover study to compare the pharmacokinetics and bioavailability of oral baclofen with an intravenous baclofen formulation. The oral formulation was a 10 mg baclofen tablet. A single intravenous dose of 5 mg was administered over 15 minutes, using the commercially available 2 mg/mL intrathecal baclofen formulation (Lioresal Intrathecal). Blood samples (6 mL) for the measurement of plasma concentrations of baclofen were collected in blood collection tubes containing K2 ethylenediaminetetraacetic acid at the following times: prior to dosing; at 5, 15, and 30 minutes; and at 1, 2, 4, 6, 8, 10, 12, and 24 hours after drug administration.

C. Determination of Baclofen Concentration in Plasma

Study plasma samples were prepared by adding 50 μL of a 500 μg/mL levetiracetam solution (internal standard) to 250 μL of K2 ethylenediaminetetraacetic acid (EDTA) human plasma. Baclofen and the internal standard were extracted from plasma by precipitating the protein with methanol and drying it under nitrogen at approximately 40° C. The dried residues were reconstituted in 300 μL of a mobile phase consisting of 20 mM ammonium acetate—methanol (75:25) solution. After 1 minute of vortex mixing, the reconstituted sample solution was filtered and injected onto the high-performance liquid chromatograph-mass spectrometer system. Standard curve samples over a range of 20 to 400 ng/mL baclofen and quality control samples containing 30 (low), 80 (medium), and 240 ng/mL (high) baclofen were prepared and analyzed in triplicate along with the study samples. The assay was linear over the range 20-400 ng/mL with a lower limit of quantification of 20 ng/mL.

Baclofen concentration—time data were analyzed using a noncompartmental pharmacokinetic approach with Phoenix software (version 6.2; Pharsight Corporation, Mountain View, CA). The terminal rate constant ($\lambda z$) was determined from the slope of the terminal log-linear portion of the plasma concentration—time curve, and the terminal half-life ($t_{1/2}$) was calculated as $\ln 2/(\lambda z)$. Maximum plasma concentrations ($C_{max}$) and time to maximum concentration ($T_{max}$) were determined by direct observation of the data. The area under the concentration-time curve to the last nonzero plasma concentration ($C_{last}$) that was above half the lower limit of quantification (10 ng/mL) was calculated by the trapezoidal rule and reported as $AUC_{last}$. The area under the concentration-time curve extrapolated to infinity ($AUC_{0-\infty}$) was calculated as $AUC_{last}+(C_{last}/\lambda z)$. Mean and standard deviation values for the parameters were also obtained using the descriptive statistics tool in Phoenix version 6.2. A paired t-test was used to determine if statistical differences existed in log normalized, dose-adjusted area under the curve between oral and intravenous arms.

D. Results

A summary of the pharmacokinetic parameters is presented in Table 1. The mean concentration-time profiles for both (5 mg intravenous and 10 mg oral) arms are shown in Table 1. When the subjects received the intravenous formulation, the observed maximum baclofen concentration occurred at the 5-minute time point, whereas the median Tmax for oral administration was 1 hour. The mean (standard deviation) Cmax values for the oral (10 mg) and intravenous (5 mg) doses were 176 (15) ng/mL and 313 (75) ng/mL, respectively (Table 1). The mean $t_{1/2}$ was similar for both the oral and intravenous arms (4 and 4.52 hours, respectively). The mean absolute bioavailability of the oral baclofen tablets (Table 1) was 74%. There was a significant difference in log-normalized, dose-adjusted area under the curves (P=0.0024) between oral and intravenous dosing with similar variability (coefficient of variation: 18%-24%).

TABLE 1

Mean ± SD of Baclofen Pharmacokinetic Parameters Following Oral (10 mg) and Intravenous (5 mg) Administration.

| Pharmacokinetic parameter | 5 mg IV (mean[a] ± SD) | 10 mg oral (mean ± SD) |
|---|---|---|
| $C_{max}$ (ng/ml) | 310 ± 74 | 174 ± 16 |
| $T_{max}$ (h)[b] | — | 1.0 (0.5-2.0) |
| $AUC_{last}$ (ng · h/mL) | 593 ± 111 | 878 ± 199 |
| $AUC_{0-\infty}$ (ng · h/mL) | 707 ± 166 | 1023 ± 232 |
| $AUC_{0-\infty}$/Dose[c] (ng · h/mL/mg) | 141 ± 33 | 102 ± 23 |
| Bioavailability (%) | | 74 ± 15 |
| $T_{1/2}$ (h) | 4.52 ± 1.6 | 4.03 ± 0.73 |

Abbreviations:
AUC, area under the curve;
IV, Intravenous;
SD, standard deviation.
[a]Mean values are presented as arithmetic means
[b]Median (min, max) reported for $T_{max}$.
[c]Two-tailed P value < .05 (paired t-test performed on dose-normalized area under the curve)

The investigational intravenous formulation was well tolerated. All treatment-emergent adverse events were characterized by the investigator as being mild in severity, and all subjects returned to their baseline values within 6 hours of drug administration.

E. Discussion

This example illustrates that absolute oral baclofen bioavailability is about 75%, indicating that approximately 25% of a 10-mg dose is either not absorbed or undergoes first-pass metabolism prior to drug reaching systemic circulation. This suggests that a smaller intravenous baclofen dose can be used when it is substituted for an oral dose. For example, assuming linear kinetics, the total systemic exposure (area under the curve) after an intravenous dose of 15 mg would be equivalent to the total exposure achieved after 20 mg of oral baclofen dose. Thus, this example suggest that when intravenous baclofen is substituted for oral baclofen, an equivalent intravenous dose will be about 75% of the oral dose.

In one embodiment of the invention, a method of converting an oral dose of baclofen to an intravenous dose of baclofen comprises (a) determining the oral dose; and (b) multiplying the oral dose by between about 0.45 and about 1.0 to determine the intravenous dose. In another embodiment of the invention, a method of converting an oral dose of baclofen to an intravenous dose of baclofen comprises (a) determining the oral dose; and (b) multiplying the oral dose by between about 0.6 and about 0.9 to determine the intravenous dose. In yet another embodiment of the invention, a method of converting an oral dose of baclofen to an intravenous dose of baclofen comprises (a) determining the oral dose; and (b) multiplying the oral dose by about 0.75 to determine the intravenous dose.

All publications, patents, and patent applications cited above are incorporated by reference herein as though fully set forth.

It will be apparent to those skilled in the art that many modifications and equivalents thereof may be made without departing from the spirit and scope of the invention.

What is claimed is:

1. A method of treating or preventing baclofen withdrawal in a human subject presently being treated with a therapeutically effective amount of oral baclofen, the method comprising:
   discontinuing oral administration of the therapeutically effective amount of baclofen to the subject;
   administering to the subject a bolus intravenous dose of solution comprising about 75% of the therapeutically effective amount of oral baclofen; and repeating administration of the bolus intravenous dose of baclofen about every 6 to 8 hours.

2. The method of claim 1, wherein the solution comprises baclofen at a concentration of about 0.5-2.0 mg/mL.

3. The method of claim 1, wherein the solution comprises baclofen at a concentration of about 0.5-1.0 mg/mL.

4. The method of claim 1, wherein the baclofen withdrawal comprises at least one of rebound increases in muscle tone, spasms, status epilepticus, hallucinations, a neuromalignant syndrome-like condition, rhabdomyolysis, and multisystem organ failure.

5. A method of treating or preventing baclofen withdrawal in a human subject presently being treated with a therapeutically effective amount of oral baclofen, the method comprising:
  discontinuing oral administration of the therapeutically effective amount of baclofen to the subject;
  administering to the subject a continuous intravenous infusion of solution comprising about 75% of the therapeutically effective amount of oral baclofen over a time period of about 24 hours.

6. The method of claim 5, wherein the solution comprises baclofen at a concentration of about 0.5-2.0 mg/mL.

7. The method of claim 5, wherein the solution comprises baclofen at a concentration of about 0.5-1.0 mg/mL.

8. The method of claim 5, wherein the baclofen withdrawal comprises at least one of rebound increases in muscle tone, spasms, status epilepticus, hallucinations, a neuromalignant syndrome-like condition, rhabdomyolysis, and multisystem organ failure.

9. A method of treating or preventing baclofen withdrawal in a human subject presently being treated with a therapeutically effective amount of oral baclofen, the method comprising:
  discontinuing oral administration of the therapeutically effective amount of baclofen to the subject;
  administering to the subject a continuous intravenous infusion of solution comprising about 75% of the therapeutically effective amount of oral baclofen; and
  continuing the infusion about every 24 hours.

10. The method of claim 9, wherein the solution comprises baclofen at a concentration of about 0.5-2.0 mg/mL.

11. The method of claim 5, wherein the solution comprises baclofen at a concentration of about 0.5-1.0 mg/mL.

12. The method of claim 9, wherein the baclofen withdrawal comprises at least one of rebound increases in muscle tone, spasms, status epilepticus, hallucinations, a neuromalignant syndrome-like condition, rhabdomyolysis, and multisystem organ failure.

* * * * *